United States Patent [19]

Wittmann

[11] 4,008,132
[45] Feb. 15, 1977

[54] PROCESS FOR THE ELECTROLYTE PREPARATION OF DIACETONE-2-KETOGULONIC ACID

[75] Inventor: Rolf Wittmann, Darmstadt, Germany

[73] Assignee: Merck Patent Gesellschaft mit beschrankter Haftung, Darmstadt, Germany

[22] Filed: Feb. 13, 1976

[21] Appl. No.: 658,034

[30] Foreign Application Priority Data

Feb. 13, 1975 Germany .......................... 2505911

[52] U.S. Cl. ................................................ 204/79
[51] Int. Cl.$^2$ ......................................... C25B 3/02
[58] Field of Search ..................................... 204/79

[56] References Cited

UNITED STATES PATENTS 2,559,033  7/1951  Verheyden .......................... 204/79
2,559,034  7/1951  Verheyden .......................... 204/79

*Primary Examiner*—R. L. Andrews
*Attorney, Agent, or Firm*—Millen & White

[57] ABSTRACT

Diacetone-2-ketogulonic acid is prepared by electrochemical oxidation of diacetone-sorbose in an aqueous alkaline medium in the presence of 0.001 to 1% of surfactant.

4 Claims, No Drawings

PROCESS FOR THE ELECTROLYTE PREPARATION OF DIACETONE-2-KETOGULONIC ACID

BACKGROUND OF THE INVENTION

Diacetone-2-ketogulonic acid can be made by electrochemical oxidation of diacetone-sorbose by passing an electrical current through an aqueous alkaline solution containing diacetone-sorbose. Diacetone-2-ketogulonic acid, an intermediate for the preparation of ascorbic acid, is obtained in relatively high yields.

However, known processes have certain disadvantages. In comparatively long electrochemical operations, current and material yields are reduced and yields of the desired end product are not reproducible.

A further disadvantage of known processes is that diacetone-sorbose used can not be oxidized quantitatively under technically and economically acceptable conditions and that, in some cases, conversions as low as about 20% of theoretical are achieved.

Good results can be achieved by adding nickel salts to the electrolyte solution but, in this process, the life of the anode is limited by accretion of voluminous deposits of nickel oxide. Also, special precautions are required to prevent toxic nickel salts remaining in the electrolyte solution from being disposed of in the waste water.

Addition of water-soluble co-solvents can prevent or retard poisoning of the cathode. In Chemie-Ingenieur-Technik, 46, (1974) pages 569-597, various organic solvents are mentioned for this purpose. However, in anodic oxidation of diacetone-sorbose, use of these solvents produces no substantial improvements. Additionally, high concentrations of added solvents have to be removed in additional process steps and possibly worked up and recycled.

SUMMARY OF THE INVENTION

This invention relates to a process of preparing diacetone-2-ketogulonic acid by electrochemical oxidation of diacetone-sorbose in an aqueous alkaline medium, comprising carrying out the electrolysis in the presence of 0.001 to 1% of a surfactant. In a preferred aspect, between 0.005 and 0.1% by weight of surfactant of total electrolyte solution is added.

The process of this invention has several advantages. Almost pure aqueous solution are used so that simple materials can be used for fabricating electrolysis cells and measures to prevent the build up of explosive solvent vapors are unnecessary. The work up is simple, since the product precipitates out in pure form so that no toxic materials remain in the waste water, which need not be worked up to recover solvents.

Surprisingly, addition of small amounts of surfactants considerably improves electrochemical oxidation of diacetone-sorbose to diacetone-2-ketogulonic acid. Evidently, electrolysis by-products which poison the electrodes are dissolved from the electrodes by the added surfactant so that substantially constant current and material yields are obtained. Moreover, the product obtained is free of diacetone-sorbose. The laborious extraction of the electrolyte solutions to remove unreacted diacetone-sorbose can thus be omitted. This is a marked technical advantage. It could not be foreseen that a well developed process could be improved so decisively in this simple manner. Initially, it was not apparent that added surfactants would not disturb the electrolysis. Surprisingly, the added surfactants also seem to dissolve or emulsify the electrolysis by-products so that diacetone-ketogulonic acid can be precipitated from the aqueous solution in especially pure form.

DETAILED DESCRIPTION

The surfactant used in the process of this invention can be neutral, amphoteric, anionic or cationic. In principle, any commonly available surfactant can be used. It is preferred that they be reasonably stable to alkalis and do not unfavorably affect the electrochemical oxidation. Thus, the added surfactant should be stable and inert under the reaction conditions employed. However, because very low concentrations of the surfactants are used, some instability in the course of the reaction does not matter substantially. One skilled in the art can, by routine experiments, find out the optimal surfactant for a given case. Because the course of the reaction is essentially independent of the surfactant employed, optimization can include selection of surfactants which decompose completely and rapidly in the waste water.

Typical of neutral surfactants which can be employed are fatty acid polyglycol ethers, alkylphenol polyglycol ethers as well as non-ionic or amphoteric surfactants. Anion-active surfactants which can be employed include soaps and modified soaps, alkyl sulfonates, alkyl aryl sulfonates, and other classes of anionic surfactants. Amine salts, quaternary ammonium salts, phosphonium salts and sulfonium salts are typical of cationic surfactants which can be used. Mixtures of various surfactants can also be used.

Neutral, non-ionic, amphoteric, cationic and anionic surfactants usable in the practice of this invention thus generally include compounds or mixtures of those types of compounds as set forth in Kirk Othmer, Vol. 19, pp. 507-593, 1969.

Exemplary of preferred surfactants are:
a. anionic surfactants
1. dodecylbenzenesulfonic acid
2. sodium dodecylbenzensulfonate
3. dioctyl sodium sulfosuccinate
4. paraffin-sulfonic acid sodium salt
5. sodium tetrapropylenebenzenesulfonate
6. sodium diisopropylnaphthalenesulfonate
7. sodium oleyl methyl tauride
b. cationic surfactants
1. N-cetyl-N,N,N-trimethylammonium bromide
2. fatty acid triethanolamine esters
3. octadecyldiethanolamine
4. lauryldipolyglycolamine
c. neutral surfactants
1. fatty acid polyglycol ether
2. nonylphenol polyglycol ether
3. fatty acid monoglycerides
4. fatty acid ethanolamides Of the alkylbenzensulfonic acid derivatives, those with an alkyl chain of 12-14 carbon atoms are particularly preferred. Of the paraffin sulfonic acid derivatives, those with 9 – 15 carbon atoms in the alkyl are preferred.

Of cationic surfactants, those are preferred in which, of $R_1R_2R_3R_4N^+X^-$, $R_1$ is of 14-28 carbon atoms and $R_2$, $R_3$ and $R_4$ are methyl or ethyl.

Neutral surfactants derived from polyethylene glycol preferably have 3-20 ethylene oxide units in the polyglycol chain. Presursor fatty acids preferably contain 8–18 carbon atoms and precursor alkylphenols 6–12 carbon atoms in the alkyl group.

Most preferred of the surfactants are dodecylbenzenesulfonic acid or sodium salt, fatty acid polyglycol ether, nonylphenol polyglycol ether, sodium oleyl methyl tauride, dioctyl sodium sulfosuccinate, sodium paraffin sulfonates, and N-cetyl-N,N,N-trimethylammonium bromide.

The process according to the invention is carried out in an electrolysis vessel which contains a cathode, and anode and possibly a diaphragm.

The electrode material is chosen from conventional materials. For the cathode, stainless steel or Monel metal as well as silver, platinum and palladium have been used. The same materials can be used as anode. Other materials also used as anode are graphite, carbon, nickel, iron or sintered metals. Sintered nickel is especially preferred for use in the process of this invention.

The electrolysis vessel can contain a diaphragm in order to prevent diacetone-sorbose or diacetone-2-ketogulonic acid being consumed in cathodic reactions. Any materials used for diaphragms should be inert to the components of the reaction mixture. Diaphragms of alkali-stable synthetic resins, such as polytetrafluoroethylene, are preferred. However, diaphragms can also be used.

The process according to the invention can also be preferably carried out in electrolysis vessels without diaphragms.

A preferred embodiment of the present invention is a process, wherein the cathode is a cylindrical stainless steel net surrounded by an anode of sintered nickel plate, the aqueous alkaline medium contains 0.05–0.8 mole/liter of diacetone-sorbose and 1.5–3 mole of alkali metal hydroxide per mole of diacetone-sorbose, and said process is carried out at 20 grad to 70 grad C., at an applied direct current of 0.2 to 10 amperes/dm.$^2$ of electrode surface area.

Some general aspects of electrolysis equipment and conditions are given in the standard work: Ullmanns Encyklopaedie der Technischen Chemie, 1955, Vol. 6, pp. 429–476 or in the Manual of Manuel M. Baizer, Organic Electrochemistry, Marcel Dekker, Inc., New York, 1973.

The process according to the invention can be carried out continuously or in batches. The electrolyte solutions can contain other additives, e.g., nickel or iron salts, as described in published German Pat. No. 1,668,203 and in accepted German Pat. No. 2,410,034.

Diacetone-sorbose is normally added in the form of an aqueous solution, so that the concentration of diacetone-sorbose in the reaction mixture is about 0.05 to 0.8 mole/l., preferably 0.1 to 0.5 mole/l. The ratio of diacetone-sorbose to alkali is generally not less than 1:1. It is expedient to select the concentrations such that the reaction mixture always contains 1.5 to 3, preferably 1.5 to 2 moles, of alkali metal hydroxide per mole diacetone-sorbose.

The aqueous solution is made alkaline by any soluble inorganic base, preferably an alkali metal hydroxide. Sodium hydroxide is most preferred.

The electrolysis is done with good stirring or circulation of the medium by pump at a temperature of 20° to 70° C., preferably 30° to 55° C., applying a direct current of 0.2 to 10, preferably 0.5 to 5, ampere per dm$^2$. of electrode surface area. The terminal voltage thereby is 1.8 to 3.0 volts, preferably 2.0 to 2.7 volts.

The period of the electrolysis depends on current strength and on the amount of diacetone-sorbose to be reacted. Assuming current yield of 100% of theory, 107.2 ampere hours (Ah) are necessary to oxidize 1 mole of diacetone-sorbose. In the process of this invention, 150 to 300 Ah are required for the oxidation of one mole of diacetone-sorbose. By optimizing the process conditions, high current yields can be achieved.

The electrolyzed reaction mixture is worked up in a known manner. The solution is, possibly after previous filtration and possibly after previous concentration, cooled to a temperature between +5° and −5° C. and acidified. A strong mineral acid, preferably concentrated hydrochloric acid is used in order to avoid increasing the volume of the solution excessively. The solution is conveniently brought to pH 2. The precipitated diacetone-2-ketogulonic acid is subsequently removed by filtration and centrifugation. The product so obtained is extraordinarily pure and thus is an especially valuable intermediate for ascorbic acid synthesis.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

A cylindrical vessel (diameter 12 cm., height 19 cm. with a stirrer, provided with a cylindrically-shaped stainless steel net as cathode surrounded at a distance of 7 mm. by an anode of sintered nickel plate (surface area 0.05 m.$^2$), is filled with 1500 ml. of an aqueous solution of 130 g. (0.5 mole) of diacetone-sorbose and 60 g. (1.5 mole) of sodium hydroxide. At a temperature of 40° C. and a terminal voltage of 2.4 V, it is electrolyzed until 80 Ah have flowed through the reaction mixture. Thereafter, the reaction mixture is cooled to 0° C., mixed with 140 –145 ml. of 32% hydrochloric acid and the resulting precipitate is filtered with suction. After washing with 200 ml. of ice water and drying at room temperature, 124 g. of diacetone-ketogulonic acid, corresponding to a yield of 84.8%, is obtained.

EXAMPLE 2

Reaction conditions of Example 1 were followed, except for addition of 0.5 ml. tetrapropylenebenzenesulfonic acid. Yield: 132 g. (90.4%).

EXAMPLE 3

Reaction conditions of Example 1 were followed, except for addition of 1 ml. of fatty acid polyglycol ether. Yield: 131.5 g. of diacetone-ketogulonic acid (90.0%).

EXAMPLE 4

Reaction conditions of Example 1 were used, except for addition of 0.1 g, of nonylphenol polyglycol ether. Yield: 134.2 g. (92.0%) of diacetone-ketogulonic acid.

EXAMPLE 5

Reaction conditions of Example 1 were used, except for addition of 0.7 g. sodium dodecylbenzenesulfonate. Yield: 130 g. (89.0%) of diacetone-ketogulonic acid.

EXAMPLE 6

Reaction conditions of Example 1 were used, except for addition of 0.34 g. sodium oleyl methyl tauride. Yield: 131 g. (89.7%) of diacetone-ketogulonic acid.

EXAMPLE 7

Reaction conditions of Example 1 were used with the addition of 1 g. of dioctyl sodium sulfosuccinate. Yield: 130 g. (89.0%) of diacetone-ketogulonic acid.

EXAMPLE 8

Reaction conditions of Example 1 were used, with the addition of 1 g. of a mixture of sodium salts of paraffin-sulfonic acids. Yield: 129.5 g. (88.7%) of diacetone-ketogulonic acid.

EXAMPLE 9

Reaction conditions of Example 1 were used, with the addition of 0.5 g. N-cetyl-N,N,N-trimethylammonium bromide. Yield: 131.5 g. (90.0%) of diacetone-ketogulonic acid.

EXAMPLE 10

Reactions conditions of Example 1 were used, with the addition of 0.02 g. nonylphenol polyglycol ether. Yield: 138.5 g. (95.0%) of diacetone-ketogulonic acid.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of diacetone-2-ketogulonic acid by electrochemical oxidation of diacetone-sorbose in an aqueous alkaline medium, comprising carrying out the electrolysis in the presence of 0.001 to 1% by weight of a surfactant.
2. The process of claim 1, wherein 0.001 to 0.1% by weight of the surfactant is present.
3. The process of claim 1, wherein the aqueous alkaline medium contains 0.05–0.8 mole/liter of diacetone-sorbose and 1.5–3 mole of alkali metal hydroxide per mole of diacetone-sorbose.
4. The process of claim 3, wherein said process is carried out at 20° to 70° C., at an applied direct current of 0.2 to 10 amperes/dm.$^2$ of electrode surface area.

* * * * *